United States Patent [19]
Walker et al.

[11] Patent Number: 5,775,876
[45] Date of Patent: Jul. 7, 1998

[54] CEILING-FAN-BLADE-MOUNTED AIR FRESHENER APPARATUS

[76] Inventors: Qwan James Walker, 2028 Titan St., Harvey, La. 70058; Christopher Williams, 3522 Vespasian #137, New Orleans, La. 70114

[21] Appl. No.: 556,591

[22] Filed: Nov. 13, 1995

[51] Int. Cl.⁶ ........................................ F04D 29/00
[52] U.S. Cl. .................. 416/62; 416/5; 416/146 R; 24/304; 55/467; 55/471; 239/56; 239/57; 261/84; 261/DIG. 65; 422/124
[58] Field of Search ................ 416/5, 62, 146 R; 261/84, DIG. 65; 239/56, 57; 422/122, 123, 124, 305; 55/467, 471, 473; D23/366–369, 377, 379, 385; 24/304

[56] References Cited

U.S. PATENT DOCUMENTS

| | | |
|---|---|---|
| D. 324,910 | 3/1992 | Portis . |
| D. 334,800 | 4/1993 | Portis . |
| 2,720,013 | 10/1955 | Clarke ............................ 416/62 |
| 2,868,489 | 1/1959 | Calcut ............................ 24/304 |
| 3,739,558 | 6/1973 | Harson .......................... D23/366 |
| 4,523,870 | 6/1985 | Spector .......................... D23/369 |
| 4,676,721 | 6/1987 | Hardee . |
| 4,753,573 | 6/1988 | McKnight ....................... 416/62 |
| 4,944,898 | 7/1990 | Glaser . |
| 5,022,819 | 6/1991 | Murcin et al. . |
| 5,370,721 | 12/1994 | Carnahan . |
| 5,383,765 | 1/1995 | Baxter et al. ................... 416/62 |

*Primary Examiner*—Edward K. Look
*Assistant Examiner*—Christopher Verdier

[57] ABSTRACT

A ceiling-fan-blade-mounted air freshener apparatus includes a housing assembly which includes a lower housing portion and an upper housing portion projecting upward from the lower housing portion. The upper housing portion includes a plurality of vent apertures. An air freshener/matrix assembly is housed within the housing assembly. A housing-to-blade connector connects the housing assembly to a ceiling fan blade. In one embodiment, the housing-to-blade connector is comprised of a layer of pressure-sensitive adhesive bonded to a bottom side of the lower housing portion. The housing-to-blade connector further includes a peel strip removably adhered to a bottom surface of the layer of pressure-sensitive adhesive. The housing assembly includes a pointed end, and the air freshener/matrix assembly includes a complementary pointed end. The pointed end of the air freshener/matrix assembly is wedged into the pointed end of the housing assembly under an influence of centrifugal force. In a second embodiment, the housing-to-blade connector is comprised of a clip assembly which includes a pair of spring clamp members which project upward from a clip base member. A centrifugal stop member projects upward from the clip base member. A layer of pressure-sensitive adhesive is bonded to a bottom side of the clip base member. A peel strip is removably adhered to a bottom surface of the layer of pressure-sensitive adhesive. A carrier assembly retains the air freshener/matrix assembly. The carrier assembly includes a pointed end.

7 Claims, 3 Drawing Sheets

FIG 3
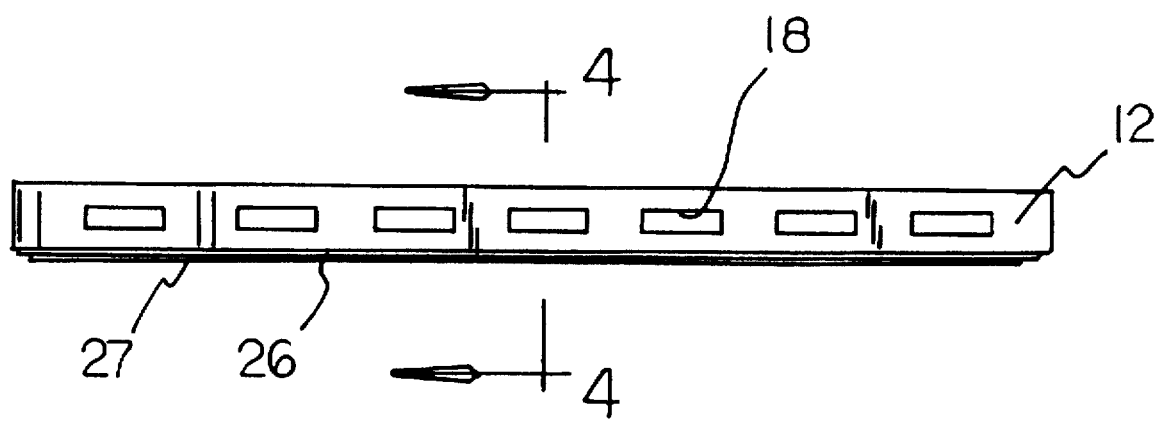
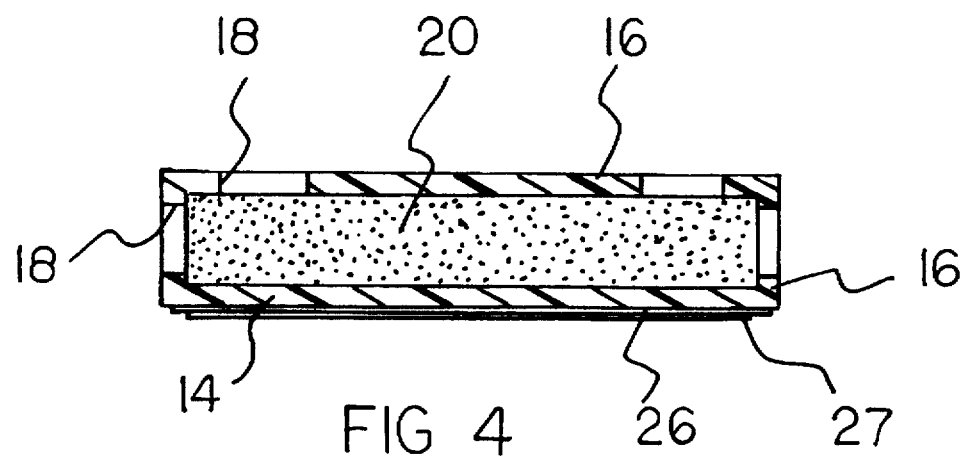
FIG 4

CEILING-FAN-BLADE-MOUNTED AIR FRESHENER APPARATUS

BACKGROUND OF THE INVENTION

1. Field of the Invention

The present invention relates generally to air fresheners and, more particularly, to air fresheners mounted on ceiling fan blades.

2. Description of the Prior Art

Air in a room often acquires a stale or otherwise unpleasant odor. As a result, various devices have been marketed which provide for freshening room air. Some rooms are equipped with one or more ceiling fans. It has been realized that the ceiling fan can be used to distribute an air freshening material as the ceiling fan operates. More specifically, U.S. Pat. No. 4,944,898 discloses an air freshener device which is mounted on a blade of a ceiling fan. One portion of the device is permanently mounted on the ceiling fan blade, and a second portion of the device is removable and replaceable on the first portion of the device. A number of disadvantages are present in using the above-mentioned device which requires that a portion of the device be permanently mounted on a ceiling fan blade. One disadvantage is that variations in positioning to bring about optimum air freshener distribution is not obtainable. Another disadvantage is that if a specific type of air freshener is discontinued, the first portion of the discontinued device remains attached to the ceiling fan blade. In this respect, it would be desirable if a ceiling-fan-blade-mounted air freshener device does not include a portion that is permanently mounted to the ceiling fan blade.

Each of U.S. Pat. Nos. Des. 334,800 and Des. 324,910 discloses a ceiling-fan-blade-mounted air freshener device which includes a mounting strap that encircles the ceiling fan blade. Because a portion of the blade-encircling mounting strap is visible in the room from below the ceiling fan blade, it would be desirable if a ceiling-fan-blade-mounted air freshener device does not employ a mounting strap that encircles the ceiling fan blade.

U.S. Pat. No. 5,022,819 discloses a spring-containing air fragrance device for a ceiling fan. The device includes two separate and distinct fan-clip-on brackets which are connected together by two separate and distinct spiral springs. All in all, a four component fan-clip-on assembly is provided. To avoid the complexities associated with a four component fan-clip-on assembly, it would be desirable if a ceiling-fan-blade-mounted air freshener device were provided with a single-component device for attaching an air freshener to a ceiling fan blade.

The following patents may also be of interest: U.S. Pat. No. 4,676,721 and U.S. Pat. No. 5,370,721. More specifically, U.S. Pat. No. 4,676,721 discloses a room air cleaner that is mounted on a ceiling fan blade. U.S. Pat. No. 5,370,721 discloses a filter that is mounted on a ceiling fan blade.

Still other features would be desirable in a ceiling-fan-blade-mounted air freshener apparatus. For example, a pressure sensitive adhesive is used to temporarily mount numerous objects on numerous surfaces. In this respect, it would be desirable if a ceiling-fan-blade-mounted air freshener device can be mounted using a pressure sensitive adhesive. Alternatively, mechanical mounting brackets using a spring action are often used for temporarily mounting numerous objects on numerous surfaces. In this respect, it would be desirable if a ceiling-fan-blade-mounted air freshener device can be mounted using a mechanical bracket having a spring action.

A ceiling fan blade has a top surface and a bottom surface. The bottom surface is visible from below the blade, and the top surface is not visible from below the blade. In order to use a ceiling-fan-blade-mounted air freshener device that is not visible by persons in the room below the blade, it would be desirable if the ceiling-fan-blade-mounted air freshener device were mounted on the top surface of the ceiling fan blade.

Thus, while the foregoing body of prior art indicates it to be well known to use ceiling-fan-blade-mounted air freshener devices, the prior art described above does not teach or suggest a ceiling-fan-blade-mounted air freshener apparatus which has the following combination of desirable features: (1) does not include a portion that is permanently mounted to the ceiling fan blade; (2) can be mounted using a pressure sensitive adhesive; (3) can be mounted using a mechanical bracket having a spring action; (4) is mounted on the top surface of the ceiling fan blade; (5) does not employ a mounting strap that encircles the ceiling fan blade; and (6) is provided with a single-component for attaching an air freshener to a ceiling fan blade. The foregoing desired characteristics are provided by the unique ceiling-fan-blade-mounted air freshener apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a ceiling-fan-blade-mounted air freshener apparatus which includes a housing assembly which includes a lower housing portion and an upper housing portion projecting upward from the lower housing portion. The upper housing portion includes a plurality of vent apertures. An air freshener/matrix assembly is housed within the housing assembly. A housing-to-blade connector connects the housing assembly to a ceiling fan blade.

In one embodiment of the invention, the housing-to-blade connector is comprised of a layer of pressure-sensitive adhesive bonded to a bottom side of the lower housing portion. The housing-to-blade connector further includes a peel strip removably adhered to a bottom surface of the layer of pressure-sensitive adhesive.

The housing assembly includes a pointed end, and the air freshener/matrix assembly includes a complementary pointed end. The pointed end of the air freshener/matrix assembly is wedged into the pointed end of the housing assembly under an influence of centripetal force.

In a second embodiment of the invention, the housing-to-blade connector is comprised of a clip assembly which includes a clip base member which includes a clamp-holding portion, a stop-holding portion, and an intermediate portion between the clamp-holding portion and the stop-holding portion. A pair of spring clamp members project upward from the clamp-holding portion of the clip base member. A centrifugal stop member projects upward from the stop-holding portion of the clip base member. A layer of pressure-sensitive adhesive is bonded to a bottom side of the clip base member. A peel strip is removably adhered to a bottom surface of the layer of pressure-sensitive adhesive. A carrier assembly retains the air freshener/matrix assembly. The carrier assembly includes a pointed end.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ceiling-fan-blade-mounted air freshener apparatus which has all of the advantages of the prior art and none of the disadvantages.

It is another object of the present invention to provide a new and improved ceiling-fan-blade-mounted air freshener apparatus which may be easily and efficiently manufactured and marketed.

It is a further object of the present invention to provide a new and improved ceiling-fan-blade-mounted air freshener apparatus which is of durable and reliable construction.

An even further object of the present invention is to provide a new and improved ceiling-fan-blade-mounted air freshener apparatus which is susceptible of a low cost of manufacture with regard to both materials and labor, and which accordingly is then susceptible of low prices of sale to the consuming public, thereby making such ceiling-fan-blade-mounted air freshener apparatus available to the buying public.

Still yet a further object of the present invention is to provide a new and improved ceiling-fan-blade-mounted air freshener apparatus which does not include a portion that is permanently mounted to the ceiling fan blade.

Still another object of the present invention is to provide a new and improved ceiling-fan-blade-mounted air freshener apparatus that can be mounted using a pressure sensitive adhesive.

Yet another object of the present invention is to provide a new and improved ceiling-fan-blade-mounted air freshener apparatus which can be mounted using a mechanical bracket having a spring action.

Even another object of the present invention is to provide a new and improved ceiling-fan-blade-mounted air freshener apparatus that is mounted on the top surface of the ceiling fan blade.

Still a further object of the present invention is to provide a new and improved ceiling-fan-blade-mounted air freshener apparatus which does not employ a mounting strap that encircles the ceiling fan blade.

Yet another object of the present invention is to provide a new and improved ceiling-fan-blade-mounted air freshener apparatus that is provides with a single-component for attaching an air freshener to a ceiling fan blade.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 3 is a side view of the embodiment of the ceiling-fan-blade-mounted air freshener apparatus of FIG. 2.

FIG. 4 is an enlarged cross-sectional view of the embodiment of the invention shown in FIG. 3 taken along line 4—4 thereof.

DESCRIPTION OF THE PREFERRED EMBODIMENT

Figure 1:
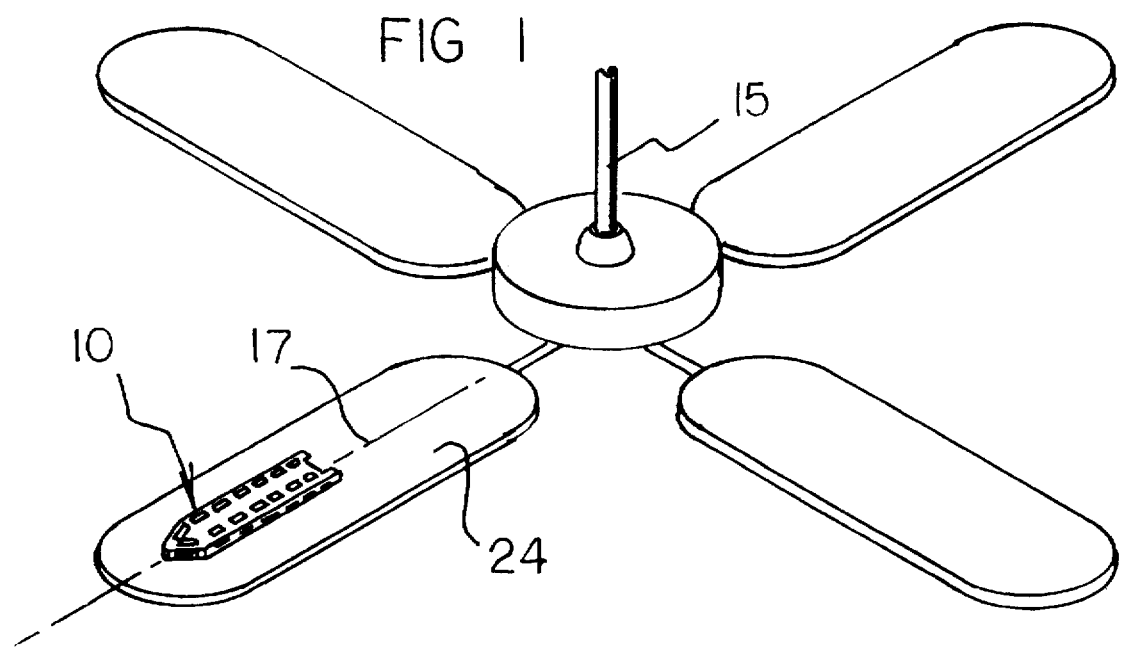
FIG. 1 is a perspective view showing a first embodiment of the ceiling-fan-blade-mounted air freshener apparatus of the invention adhesively attached to the top surface of a ceiling fan blade.
Figure 2:
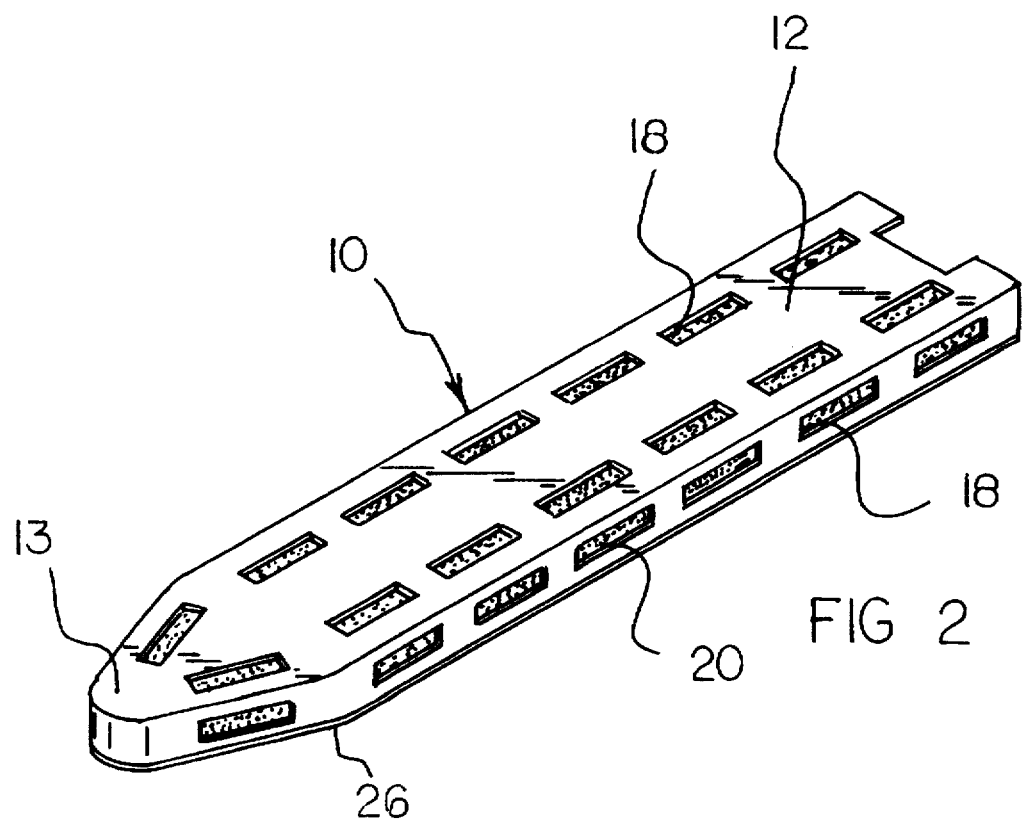
FIG. 2 is an enlarged perspective view of the embodiment of the ceiling-fan-blade-mounted air freshener apparatus shown in FIG. 1 removed from the ceiling fan blade.

With reference to the drawings, a new and improved ceiling-fan-blade-mounted air freshener apparatus embodying the principles and concepts of the present invention will be described.

Turning to FIGS. 1–4, a first embodiment of the ceiling-fan-blade-mounted air freshener apparatus of the invention generally designated by reference numeral 10. The ceiling-fan-blade-mounted air freshener apparatus 10 includes a housing assembly 12 which includes a lower housing portion 14 and an upper housing portion 16 projecting upward from the lower housing portion 14. The upper housing portion 16 includes a plurality of vent apertures 18. An air freshener/matrix assembly 20 is housed within the housing assembly 12. A housing-to-blade connector connects the housing assembly 12 to a ceiling fan blade 24.

In one embodiment of the invention, the housing-to-blade connector is comprised of a layer of pressure-sensitive adhesive 26 bonded to a bottom side of the lower housing portion 14. The housing-to-blade connector further includes a peel strip 27 removably adhered to a bottom surface of the layer of pressure-sensitive adhesive 26.

Figure 5:
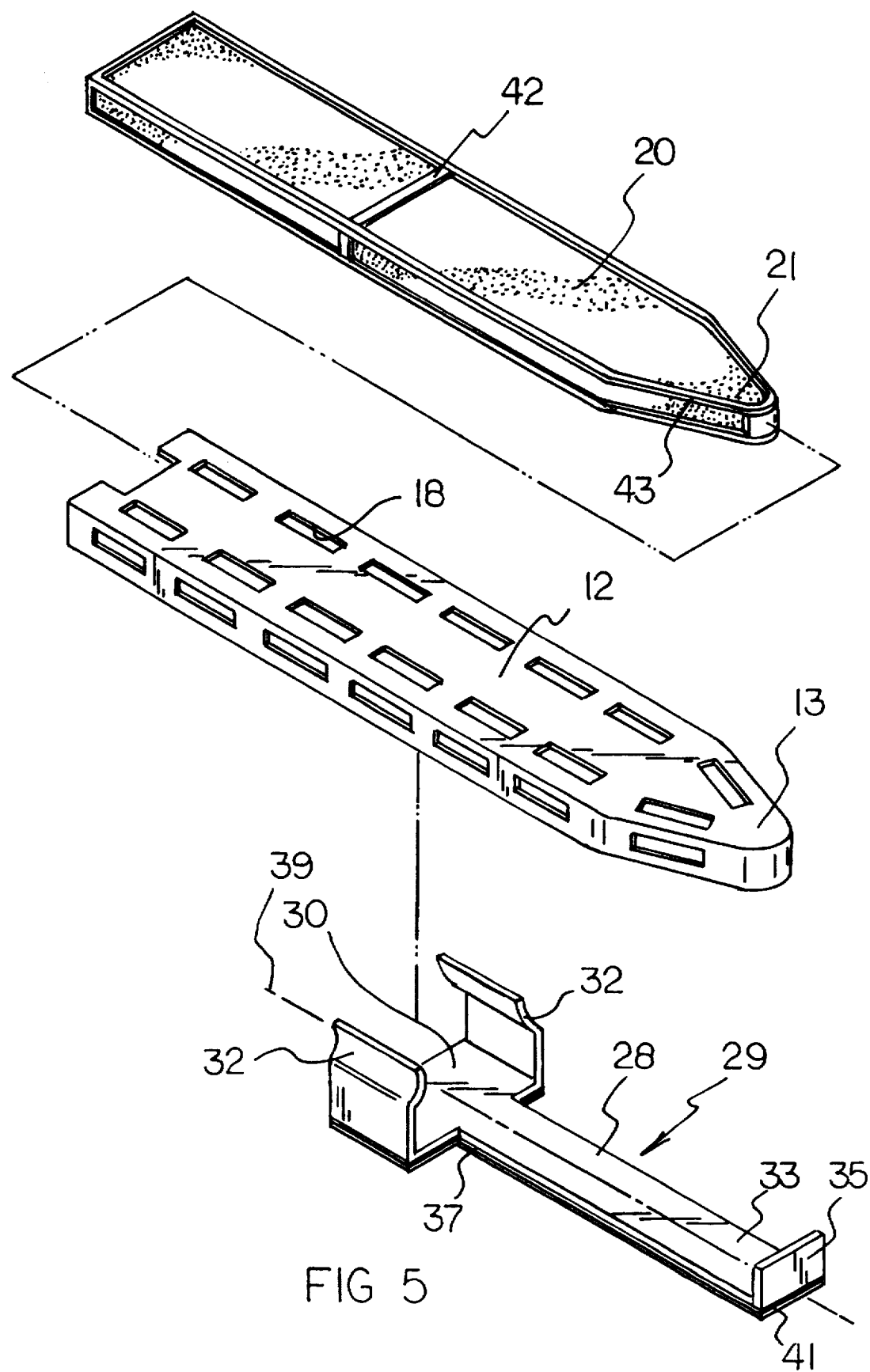
FIG. 5 is an exploded perspective view of a second embodiment of the invention which includes a spring clip which includes a pressure-sensitive adhesive for attaching the embodiment of the invention to a ceiling fan blade.

The housing assembly 12 includes a pointed end 13, and the air freshener/matrix assembly 20 includes a complementary pointed end 21 as shown in FIG. 5. The pointed end 21 of the air freshener/matrix assembly 20 is wedged into the pointed end 13 of the housing assembly 12 under an influence of centrifugal force.

In using the first embodiment of the ceiling-fan-blade-mounted air freshener apparatus 10 of the invention, the peel strip 27 is first removed from the bottom of the layer of pressure-sensitive adhesive 26. Then the layer of pressure-sensitive adhesive 26 is pressed onto the top surface of a ceiling fan blade 24. The ceiling-fan-blade-mounted air freshener apparatus 10 of the invention is positioned on the ceiling fan blade 24 so that the pointed end 13 of the housing assembly 12 is pointed away from shaft 15 of the fan. Preferably, the longitudinal axis 17 of the ceiling-fan-blade-mounted air freshener apparatus 10 is placed in alignment with a radius of a circle has the fan shaft 15 as the center of the circle when the layer of pressure-sensitive adhesive 26 is adhered to the ceiling fan blade 24. Simultaneously, the longitudinal axis 17 of the ceiling-fan-blade-mounted air freshener apparatus 10 is placed in alignment with a line bisecting the ceiling fan blade 24.

As the ceiling fan blade 24 rotates around the fan shaft 15, centrifugal force wedges the air freshener/matrix assembly 20 into the housing assembly 12. More specifically, the pointed end 21 of the air freshener/matrix assembly 20 is wedged into the pointed end 13 of the housing assembly 12.

The air freshener/matrix assembly 20 contains a quantity of odiferous material contained in a matrix portion of the air freshener/matrix assembly 20. The matrix portion can be a porous foam material. The matrix material can also be made of fibrous material such a paper or cotton. The odiferous material can be any conventional perfume or air freshener formulation. The odiferous material permeates through the vent apertures 18 into the room. This happens whether the fan is rotating or not. Of course, a greater amount of odiferous material permeates from the vent apertures 18 into the room when the fan is rotating.

Turning to FIG. 5, a second embodiment of the invention is shown. Reference numerals are shown that correspond to like reference numerals that designate like elements shown in the other figures. In addition, the housing-to-blade connector is comprised of a clip assembly 29 which includes a clip base member which includes a clamp-holding portion 30, a stop-holding portion 33, and an intermediate portion 28 between the clamp-holding portion 30 and the stop-holding portion 33. A pair of spring clamp members 32 project upward from the clamp-holding portion 30 of the clip base member. A centrifugal stop member 35 projects upward from the stop-holding portion 33 of the clip base member. A layer of pressure-sensitive adhesive 37 is bonded to a bottom side of the clip base member. A peel strip 41 is removably adhered to a bottom surface of the layer of pressure-sensitive adhesive 37.

A carrier assembly 42 retains the air freshener/matrix assembly 20. The carrier assembly 42 includes a pointed end 43. The pointed end 43 of the carrier assembly 42 accommodates the pointed end 21 of the air freshener/matrix assembly 20 and the pointed end 13 of the housing assembly 12.

In using the second embodiment of the ceiling-fan-blade-mounted air freshener apparatus 10 of the invention, the clip assembly 29 is grasped, and the peel strip 41 is pulled off of the layer of pressure-sensitive adhesive 37. The longitudinal axis 39 of the clip assembly 29 is placed in alignment with a line that bisects the ceiling fan blade 24. The layer of pressure-sensitive adhesive 37 is pressed against the top surface of the ceiling fan blade 24 to secure the clip assembly 29 thereon. Then the housing assembly 12 is clipped onto the clip assembly 29. The spring clamp members 32 of the clip assembly 29 clamp the housing assembly 12 onto the clip assembly 29. The pointed end 13 of the housing assembly 12 is placed up against the centrifugal stop member 35. Then the carrier assembly 42, which contains the air freshener/matrix assembly 20, is slid into the housing assembly 12. When the ceiling fan spins on its shaft 15, centrifugal force that is developed causes the carrier assembly 42 and the air freshener/matrix assembly 20 to be wedged into the pointed end 13 of the housing assembly 12. In addition, centrifugal force causes the housing assembly 12 to be pushed up against the centrifugal stop member 35.

The carrier assembly 42 and the retained air freshener/matrix assembly 20 can be made as a removable and replaceable cartridge unit. If desired, a removable and replaceable cartridge can also include the housing assembly 12 in addition to the carrier assembly 42 and the air freshener/matrix assembly 20.

The components of the ceiling-fan-blade-mounted air freshener apparatus of the invention can be made from inexpensive and durable plastic and paper materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved ceiling-fan-blade-mounted air freshener apparatus that is low in cost, relatively simple in design and operation, and which may advantageously be used without including a portion that is permanently mounted to the ceiling fan blade. With the invention, a ceiling-fan-blade-mounted air freshener apparatus is provided which can be mounted using a pressure sensitive adhesive. With the invention, a ceiling-fan-blade-mounted air freshener apparatus is provided which can be mounted using a mechanical bracket having a spring action. With the invention, a ceiling-fan-blade-mounted air freshener apparatus is provided which is mounted on the top surface of the ceiling fan blade. With the invention, a ceiling-fan-blade-mounted air freshener apparatus is provided which does not employ a mounting strap that encircles the ceiling fan blade. With the invention, a ceiling-fan-blade-mounted air freshener apparatus is provided which is provides with a single-component for attaching an air freshener to a ceiling fan blade.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the foregoing Abstract provided at the beginning of this specification is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A ceiling-fan-blade-mounted air freshener apparatus, comprising:

a housing assembly which includes a lower housing portion and an upper housing portion projecting upward from said lower housing portion, wherein said upper housing portion includes a plurality of vent apertures, an air freshener/matrix assembly housed within said housing assembly, and a housing-to-blade connector for connecting said housing assembly to a ceiling fan blade, and wherein:
   said housing assembly includes a pointed end,
   said air freshener/matrix assembly includes a pointed end, and
   said pointed end of said air freshener/matrix assembly is wedged into said pointed end of said housing assembly under an influence of centrifugal force.

2. The apparatus of claim 1 wherein said housing-to-blade connector is comprised of a layer of pressure-sensitive adhesive bonded to a bottom side of said lower housing portion.

3. The apparatus of claim 2 wherein said housing-to-blade connector further includes a peel strip removably adhered to a bottom surface of said layer of pressure-sensitive adhesive.

4. The apparatus of claim 1 wherein said housing-to-blade connector is comprised of a clip assembly which includes:

a clip base member which includes a clamp-holding portion, a stop-holding portion, and an intermediate portion between said clamp-holding portion and said stop-holding portion, a pair of spring clamp members projecting upward from said clamp-holding portion of said clip base member, a centrifugal stop member projecting upward from said stop-holding portion of said clip base member, and a layer of pressure-sensitive adhesive bonded to a bottom side of said clip base member.

5. The apparatus of claim 4, further including:

a peel strip, said peel strip being removably adhered to a bottom surface of said layer of pressure-sensitive adhesive.

6. The apparatus of claim 1, further including:

a carrier assembly which retains said air freshener/matrix assembly.

7. The apparatus of claim 6 wherein said carrier assembly includes a pointed end.

* * * * *